(12) United States Patent
Hollander

(10) Patent No.: US 8,631,985 B2
(45) Date of Patent: Jan. 21, 2014

(54) RESPIRATORY FACE MASK DISPENSED FROM CONTINUOUS ROLL AND METHOD FOR MAKING THE SAME

(76) Inventor: David Hollander, Brooklyn, NY (US)

( * ) Notice: Subject to any disclaimer, the term of this patent is extended or adjusted under 35 U.S.C. 154(b) by 575 days.

(21) Appl. No.: 12/926,352

(22) Filed: Nov. 12, 2010

(65) Prior Publication Data

US 2011/0114690 A1      May 19, 2011

Related U.S. Application Data

(60) Provisional application No. 61/281,171, filed on Nov. 14, 2009.

(51) Int. Cl.
*B26F 3/02*      (2006.01)
*A61B 19/02*      (2006.01)

(52) U.S. Cl.
USPC .......................................... 225/93; 206/438

(58) Field of Classification Search
USPC .......... 225/93, 100, 3, 96; 206/438; 428/684; 493/355, 342, 369, 361, 403, 404, 363, 493/324, 340; 162/194, 109, 110, 197, 286; 83/651.1, 856
See application file for complete search history.

(56) References Cited

U.S. PATENT DOCUMENTS

| | | | | |
|---|---|---|---|---|
| 3,026,239 A | * | 3/1962 | Porter | 156/750 |
| 3,835,754 A | * | 9/1974 | Lewyckyj | 493/346 |
| 4,601,592 A | * | 7/1986 | Jatczak et al. | 384/564 |
| 4,726,365 A | * | 2/1988 | Jablonski | 128/202.13 |
| 2005/0079379 A1 | * | 4/2005 | Wadsworth et al. | 428/684 |

\* cited by examiner

*Primary Examiner* — Ghassem Alie
(74) *Attorney, Agent, or Firm* — Novak Druce Connolly Bove + Quigg LLP

(57) ABSTRACT

A respirator mask dispensing system is provided. It includes a carrier material and a plurality of respirator masks mounted in parallel on the carrier material by an adhesive. The carrier material is deformed between adjacent ones of the plurality of respirator masks, the deformation being configured to assist in the tearing of the carrier material at points of deformation. The carrier material with the plurality of respirator masks as mounted therein is wound on the central core member to provide a continuous roll The adhesive bonds more strongly with the respirator masks than the carrier material such that when an individual respirator mask is removed from the carrier material the adhesive will separate from the carrier material and remain attached to the individual respirator mask.

13 Claims, 4 Drawing Sheets

RESPIRATORY FACE MASK DISPENSED FROM CONTINUOUS ROLL AND METHOD FOR MAKING THE SAME

CROSS REFERENCE TO RELATED APPLICATIONS

The present application claims priority to U.S. Provisional Patent application 61/281,171 entitled Respiratory Face Mask Dispensed From Continuous Roll, filed on Nov. 14, 2009, the disclosure of which is expressly incorporated by reference herein in its entirety.

BACKGROUND OF THE INVENTION

1. Field of the Invention

The present invention relates to a respiratory face mask. More specifically, the present invention relates to a plurality of respiratory face masks that are mounted on a carrier material and dispensed from a wound continuous roll of carrier material.

2. Discussion of Background Information

Various types of filtering face-piece respirators and masks are designed to protect the wearer from inhaling harmful particulates and dust. An air purifying respirator is a particular type facial mask that is specifically designed to filter contaminants out of the air as it flows through filter media of the mask. (This differs from, for example, a surgical mask, which is designed to block the flow of fluids between a health professional and a patient, but which provides negligible filtration of the passage of air through the surgical mask itself.)

There is a continuing need to increase prevention of the spread of disease caused by infected airborne droplets and aerosols, particularly in healthcare and clinical environments. The Center for Disease Control and Prevention has stated its concern about extending respiratory protection to patients, visitors, and other persons in the healthcare setting, in addition to healthcare workers. For example, in order to prevent transmission of communicable respiratory diseases like influenza, the CDC suggests the use of respirator masks rated N95, N99, or N100 (per U.S. standards, the "N" number rating means that the mask will stop that percentage of particles 0.3 microns or larger in size, thus N95 is rated to stop 95% of particles 0.3 microns or larger).

Prior art tight-fitting face—piece respirator masks for health environments generally fall into two categories. The first is a flexible mask, which includes an expandable air permeable filter with one or more straps that the user secures around the head and neck. These types of masks are typically individually available in a polyethylene container.

The other category of respirator masks is a semi-rigid air permeable filter material that is preformed into a cup shape with one or more straps that secure the cup over the mouth and nose of the wearer. Due to the preformed semi-rigid shape, there is little option for customization of the fit of the mask to the wearer. The mask may thus have a particular N rating based on its material, but in practice the effective N rating can be substantially lower due to a poor fit over the face of the wearer. The preformed semi-rigid shape also requires that these types of masks be formed individually and packaged in a nesting format, which is a cumbersome manufacturing process.

The current state of the art lacks a type of tight-fitting face-piece respirator mask that is easily customizable to the face of the user and can be packaged, transported and dispensed in a expeditious and low cost manner.

SUMMARY

Embodiments of the present invention describes a system and method for reducing the risk to persons by facilitating the dispensing of high performance protective face masks from surface-mounted point of service delivery systems on demand. Point of service delivery would provide greater access and convenience at reduced cost, and thus likely result in increased use by a wider range of people at risk in healthcare settings.

According to an embodiment of the invention, a respirator mask dispensing system is provided. It includes a carrier material and a plurality of respirator masks mounted in parallel on the carrier material by an adhesive. The carrier material is deformed between adjacent ones of the plurality of respirator masks, the deformation being configured to assist in the tearing of the carrier material at points of deformation. The carrier material with the plurality of respirator masks as mounted therein is wound on the central core member to provide a continuous roll The adhesive bonds more strongly with the respirator masks than the carrier material such that when an individual respirator mask is removed from the carrier material the adhesive will separate from the carrier material and remain attached to the individual respirator mask.

The above embodiment may have various features. The individual respirator mask may be dispensed by unrolling the carrier material to extend the individual respirator mask from the continuous roll, tearing the carrier material along the adjacent deformation to release a single sheet of carrier material with the individual respirator mask thereon, and separating the individual respirator mask from the torn single sheet of carrier material. The adhesive may be positioned on the plurality of masks at least as strips with uniform thickness along the lateral sides of the plurality of masks. The strips may be parallel to the dispensing direction of the continuous roll. The adhesive may be positioned on the plurality of masks as at least one island proximate to an under the chin portion on the plurality of masks. Each of the plurality of masks may have first and second notches proximate to an under the chin portion of the masks that separates the under the chin portion of the masks into first, second and third sections, the second section being coextensive with an area under the chin of a wearer, and the first and third sections can be at least partially overlapped onto the second section to form a seal on a lower jaw of a wearer. Each of the plurality of masks may have a wire generally disposed in a bridge of nose portion of the masks, the wire being deformable. The wire may be perpendicular to the dispensing direction of the continuous roll. The individual respirator mask may be dispensed by unrolling the individual respirator mask and underlying carrier material, tearing the underlying carrier material along the adjacent deformation to release the individual respirator mask with a corresponding sheet of carrier material, and individually sealing the individual respirator mask with a corresponding sheet of carrier material within packaging. The plurality of respirator masks may be mounted on the carrier medium are separated from each other. The plurality of respirator masks may be connected to each other, and delineated by deformations configured to assist in tearing an individual respirator mask free from the plurality of respirator masks. The deformations may include perforations or notches in the lateral sides of the continuous roll of carrier material.

According to another embodiment of the invention, a respirator mask packaging system, is provided. A sheet of carrier material is provided, and a respirator mask is mounted on the sheet of carrier material by an adhesive. The mask includes a deformable support along a bridge of the nose section of the respirator mask; the adhesive being positioned on the mask at least: as lateral strips along the lateral sides of the mask; and at least one island along an under the chin area of the mask. The adhesive bonds more strongly with the respirator masks than the carrier material such that when an individual respirator mask is removed from the carrier material the adhesive will separate from the carrier material and remain attached to the individual respirator mask.

The above embodiment may have various optional features. The respirator mask may have first and second notches proximate to an under the chin portion of the respirator mask that separates the under the chin portion of the respirator mask into first, second and third sections, the second section being coextensive with an area under the chin of a wearer, and the first and third sections can be at least partially overlapped onto the second section to form a seal on a lower jaw of a wearer. A plurality of the respirator mask packaging systems may be provided in which each sheet of carrier material is connected together, and collectively wound about a core member to form a continuous roll of carrier material. The continuous roll of carrier material may be deformed along lines perpendicular to the dispensing direction of the continuous roll, the individual sheets of carrier material being defined by the deformations. The deformations may include perforations or notches in the lateral sides of the continuous roll of carrier material.

Other exemplary embodiments and advantages of the present invention may be ascertained by reviewing the present disclosure and the accompanying drawings.

BRIEF DESCRIPTION OF THE DRAWINGS

The present invention is further described in the detailed description which follows, in reference to the noted plurality of drawings by way of non-limiting examples of certain embodiments of the present invention, in which like numerals represent like elements throughout the several views of the drawings, and wherein.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
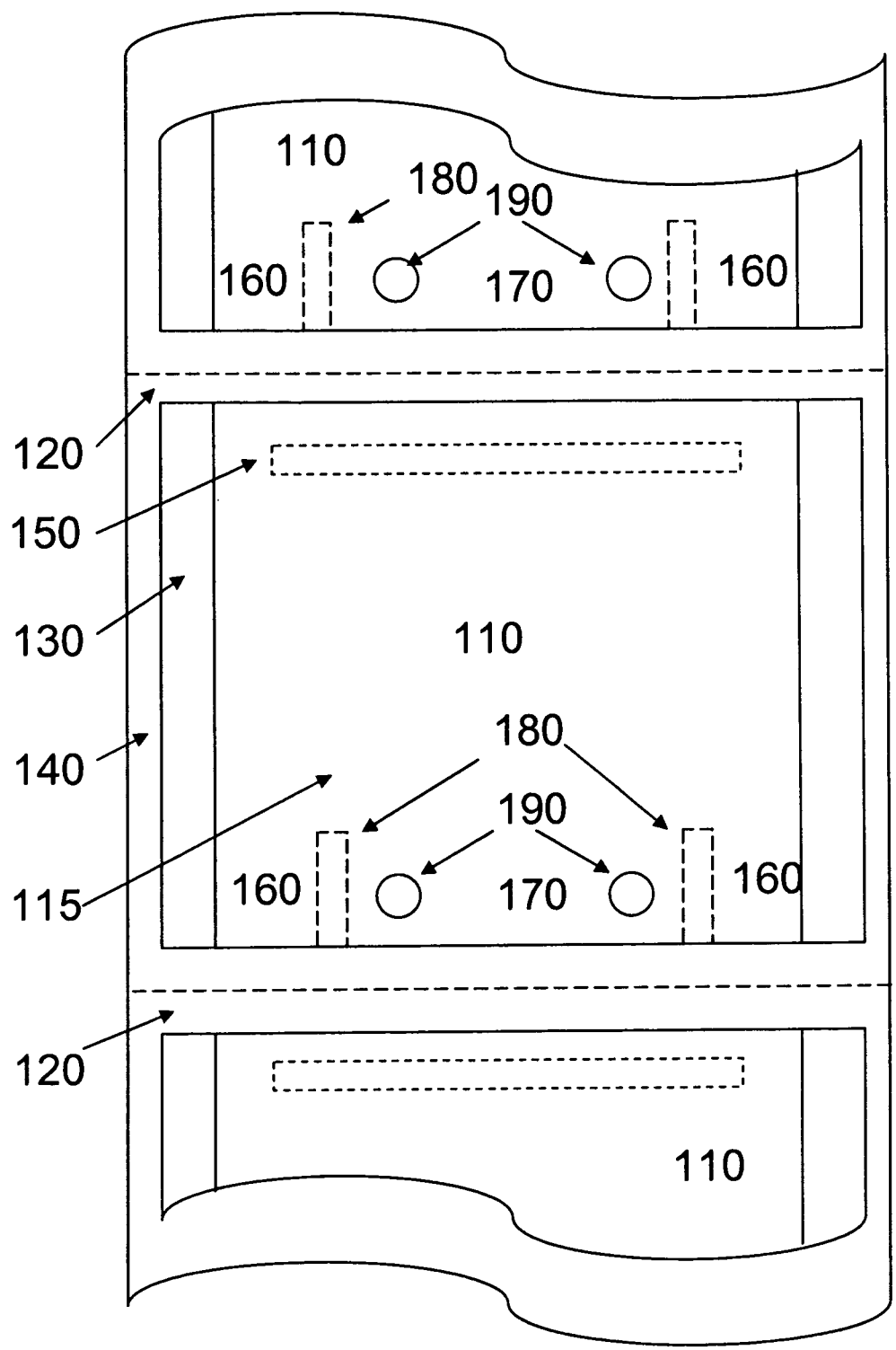
FIG. 1 illustrates a front view of an embodiment of the invention.

Referring now to FIG. 1, an embodiment of the invention is shown. A series of respirator masks 110 are mounted in parallel on an underlying carrier material 140. The entirety of one mask 110 is shown in the center of FIG. 1, while portions of adjacent masks 110 are shown above and below along carrier material 140. FIG. 1 thus shows three masks 110, although it is to be understood that carrier material 140 extends for some distance and can support as many masks 110 as are desired and/or feasible (taking into account thickness and weight considerations); an overall length of carrier material 140 on the order of 25-50 feet is preferable, but the invention is not limited to any particular length.

Figure 2:
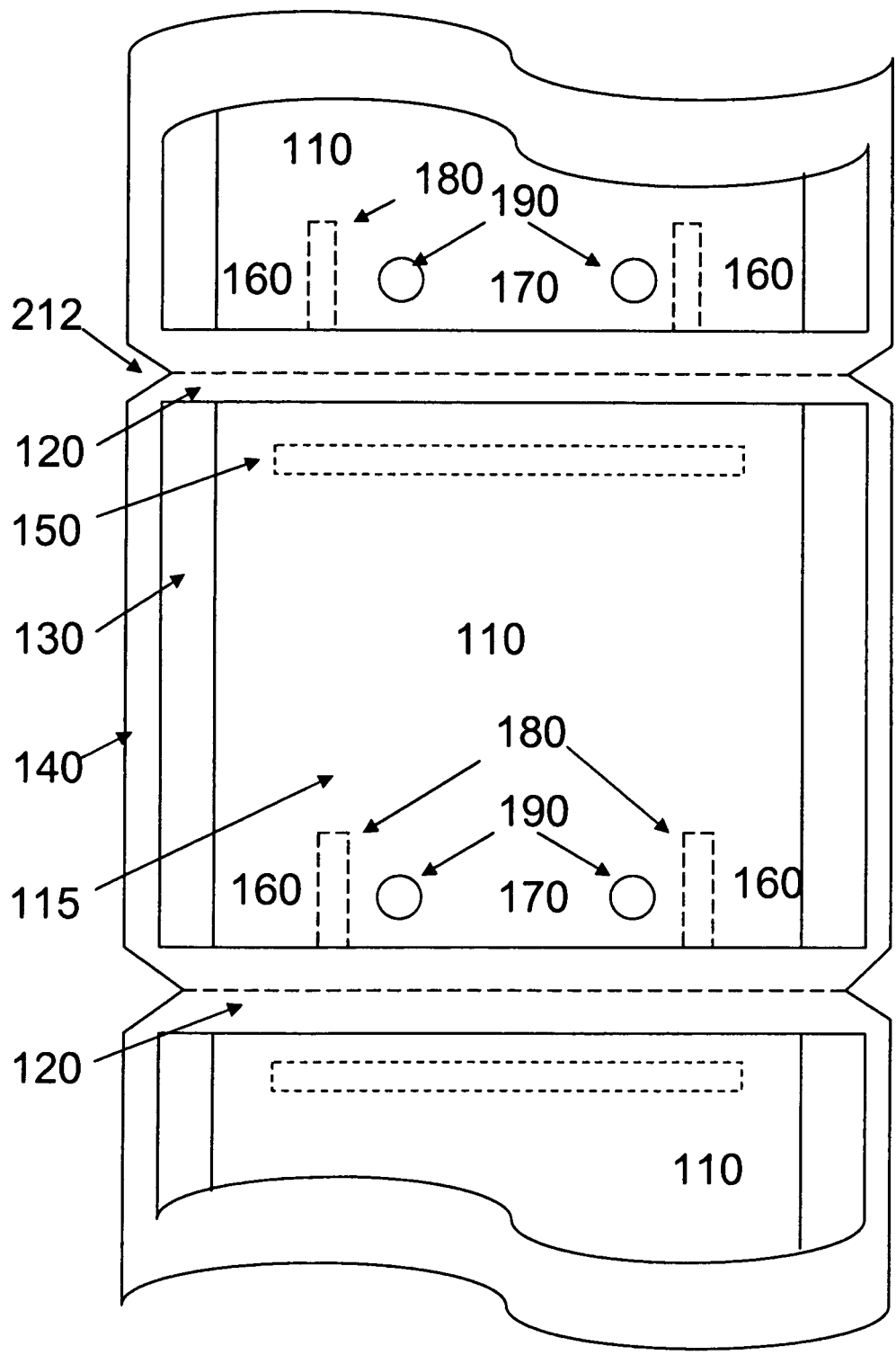
FIG. 2 illustrates a front view of an embodiment of the invention with notches.

Carrier material 140 is preferably perforated between adjacent masks 110 along line 120 so that individual masks 110 and the corresponding sheet of carrier material 140 can be easily torn free for individual use. As shown in FIG. 2, notches 212 may supplement perforations along line 120. In the alternative, notches 212 can be provided without perforations. Other deformations of carrier material 140 could also be used, such as scoring or a crease in the carrier material 140.

Carrier material 140 and mounted masks 110 are for package and dispensing purposes preferably wound into a roll around a core member, akin to the manner in which paper towels are wound around a cardboard tube. The core member (show in FIG. 3 at 325) of the instant embodiment is preferably made of a medium such as plastic that does not foster bacterial or viral growth if exposed to contaminants, although other materials could be used. The core member may be hollow so that it can be mounted on a dispenser, or include some of or the entire dispenser itself The invention is not limited to any particular type of mounting methodology. In this manner, respirator masks 110 can be packaged, transported and dispensed in the same manner as paper towels.

Each respirator mask is made from air permeable flexible filter media 115. The filter media 115 could be single flat layer, multiple layers of the same or different sub-materials, and/or overlapping layers. Filter media 115 preferably meets at least N95 standards, although lower rated masks may be acceptable for other environments such as construction sites to block out inhalation of dust and airborne debris. Electrostatically charged melt blown polypropylene fibers may be appropriate material for filter media 115. Certain types of paper or non-woven material may also be appropriate. The specific types of materials that provide the noted degrees of filtration are known to those of skill and are not discussed in further detail herein.

The mask 110 includes adhesive that preferably both secure the masks 110 to the carrier material 140 and will later secure the mask 110 to the face of the wearer. The embodiment of FIG. 1 shows the adhesive as adhesive strips 130 and adhesive islands 190. Adhesive strips 130 preferably align with the left and right sides of mask 110 and run the full length thereof; these strips 130 will later attach the lateral sides of mask 110 to the wearer's face. Adhesive islands 190 will later attach under the wearer's chin. Double sided tape is a non-limiting example of an appropriate adhesive, such as 3M brand 9828, 9917, 1522, or 9874.

The adhesive, carrier material 140 and mask 110 are preferably made from a collection of materials for which the adhesive will only lightly bond to carrier 140, but more tightly bond to the mask 110; thus when the mask 110 is removed from carrier material 140 the adhesive will separate from carrier material 140 and remain on mask 110 for later bonding with the wearer's face. Similarly, the adhesive must sufficiently bond with the wearer's face so as to maintain a seal and resist removal from light (accidentally applied) pressure, but which will yield under sufficient pressure for removal without discomfort to the wearer; adhesives used in medical contexts (such as 3M brand 9828 9917, 1522, or 9874 double sided medical tape) may be appropriate. By way of non-limiting example, mask 110 may be of an appropriate N95 paper based material, the adhesive may be a medical double sided tape, and the carrier material 140 may be of the same type of materials used between layers of double sided tape (e.g., a silicone coated or infused material, plastic, poly coated paper or Kraft liner).

The nature and location of adhesive 130 and 190 in FIG. 1 is merely exemplary. For example, Adhesive island 190 could be a single patch of adhesive or more than two patches. Other configurations of adhesive could also be used.

Adhesive 130 and 190 are preferably the same material and/or located symmetrically on mask 110, but this need not be the case and the invention is not so limited. For example, two different adhesives could be used—one that bonds more strongly with mask 110 and will remain with mask 110 when separated from carrier material 140, and a second adhesive with bonds more strongly with carrier material 140 and will remain with carrier material 140 when separated from mask 110. A similar effect could be achieved using the same adhesive but using different materials to make up carrier material 140 and/or mask 110, although this would be a more expensive solution.

Mask 110 preferably includes a horizontally positioned deformable plastic or metal wire, strip or clip 150 ("wire 150") that is perpendicular to the direction in which masks 110 are dispensed from the continuous roll. Wire 150 is preferably attached to mask 110 and sandwiched between mask 110 and carrier material 140, although the wire 150 may be on the outer side of mask 110 and/or embedded (e.g., woven into) mask 110. Wire 150 retains its original flat elongated shape absent deforming pressure, but will deform into and retain a new shape under sufficient deforming pressure. Wire 150 will generally align with the wearer's face across the bridge of the nose, and can be deformed by the wearer to contour to the bridge of the nose and the upper cheek bones.

Mask 110 preferably includes notches 180 at the lower portion thereof, which separates the lower portion of mask 110 into an under the chin section 170 and flaps 160. The under the chin section 170 will attach under the wearer's chin due to the presence of adhesive islands 190.

The mask 110 is preferably applied to the wearer's face by placing the wire 150 proximate to the bridge of the nose and deforming it into shape. Pressure is then applied to the upper and middle portions of lateral adhesive strips 130 to form and adhesive seal with the face along the cheeks, while the flaps 160 extend below the chin. The under the chin section 170 is lowered into a position first over and then under the chin with adhesion via adhesive islands 190. The wearer then pulls the flaps 160 laterally to cross over and overlap the under the chin section 170, and applies pressure to the lower portion of strips 130 to create a seal. This last step causes flaps 160 to fold over a portion of under chin section 170, thus securing the bottom of mask 110 over the user's chin and forward jaw.

Flaps 160 tend to retain sufficient flexibility to act as valves. When the wearer exhales, flaps 160 will expand away from the face and allow air to exit at least at the border of notch 180 without the exhaled air necessarily having to pass through the filtering media 115. When the wearer inhales, the negative pressure will pull flaps 160 toward the face to reassert the seal, forcing incoming inhaled air to pass through the filtering media 115. Notches 180 may be of any width, including zero (for which the notch is essentially just a cut in the media 115).

The embodiment of FIG. 1 is preferably formed using an in-line continuous rotary web process. Carrier material 140 is provided by its own continuous roll which is fed into a mechanism for supporting masks 110. Masks 110 are themselves formed from a continuous roll of media 115 which is cut to appropriate shape for individual masks 110; for stability purposes, the notches 180 can be formed on the leading edge of the media 115 before it is cut to size. The wire 150 may be added before or after the mask is cut from the roll of media 115. Adhesive for areas 130 and 190 may be applied directly to the roll of carrier material 140 before the mask 110 is mounted thereto, or applied directly to the mask 110 before it is mounted; some adhesive on the carrier material 140 and some on the mask 110 before mounting is also possible. For alignment purposes, carrier material 140 is preferably perforated after the leading and trailing mask are mounted, although it could be done before either mask 110 is applied, or after one mask 110 is mounted but before the adjacent mask 110 is mounted.

Figure 3:
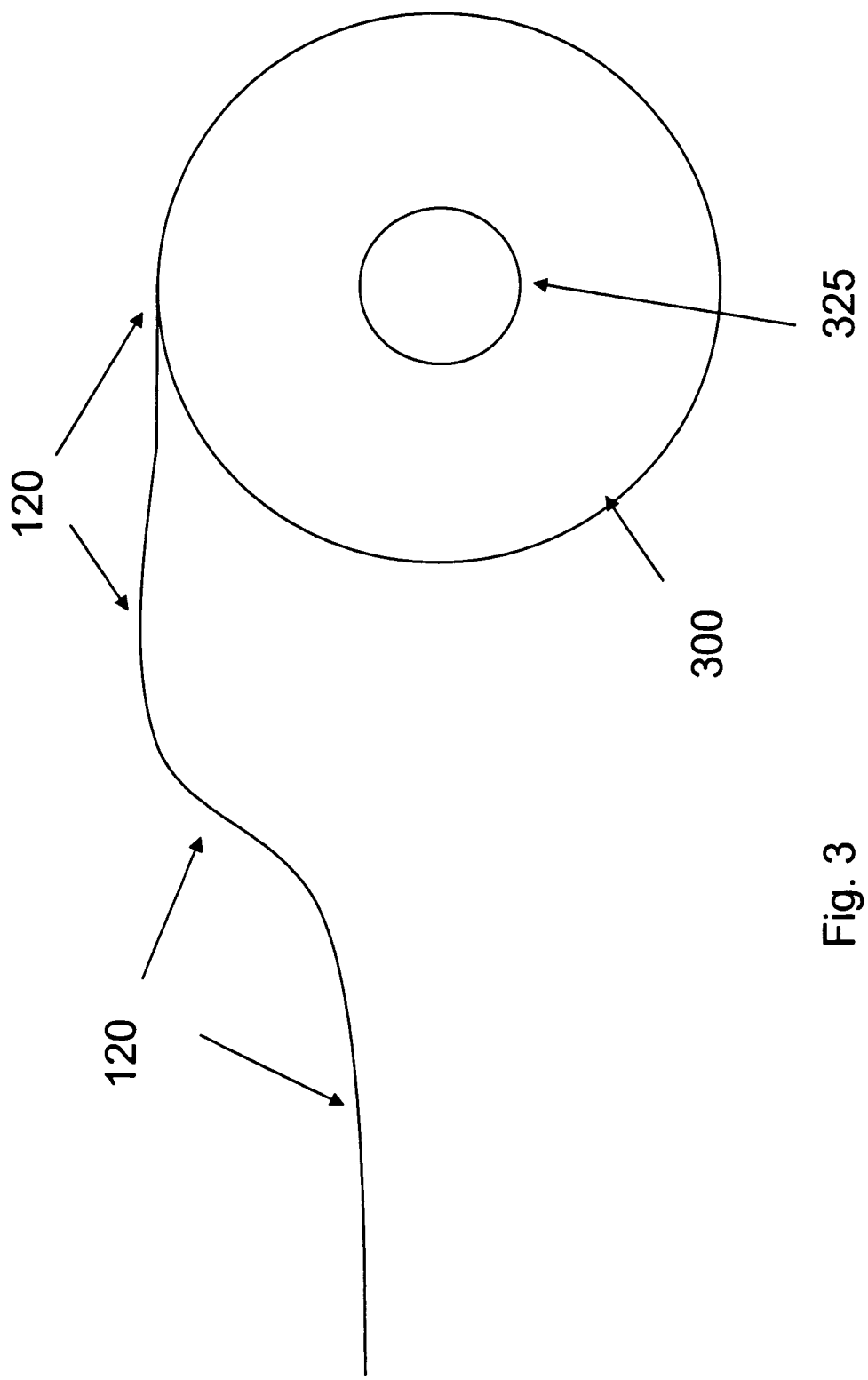
FIG. 3 illustrates a side view of masks supported by a continuous roll of wound carrier material.

FIG. 3 shows the embodiment of FIG. 1 as a continuous roll 300, with several of the closest front masks 110 dispensed (delineation is shown by indication of lines 120). The embodiment of FIG. 3 shows the continuous roll 300 supported about a hollow core member 325, which may be a plastic tube. As noted above, there are various methodologies that could be used for mounting the continuous roll 300.

Roll 300 may be manufactured individually. In the alternative, several individual rolls 300 could be manufactured as a common roll, whereupon individual rolls are cut from the larger common roll.

The rotary web process enables the mask to be produced in volume at high throughput speed, which reduces production cost. A material perforated at various intervals is used as both a carrier material 140 and mask media 115, so that when the mask 110 is dispensed from the roll it can first be separated from the roll, and then easily pulled apart and removed from the carrier for instant application.

The masks 110 could be packaged and sold for use in the continuous roll format as shown in FIG. 3. In the alternative, the mask could be individually cut at the production end, packaged individually, and dispensed as individual masks using the same rotary web process.

Adhesive strips 130, adhesive islands 190, and notches 180 are preferably of uniform thickness and aligned along common longitudinal axis for the length of the continuous roll 300. Throughput speed is increased and waste minimized by applying adhesive only to the lateral side edges of the mask 110 in continuous line with the direction of the web process, and in conjunction with utilizing other methods of adapting the mask 110 to the contours of the user's face across the top and bottom of the mask. In the alternative, masks 110 could be oriented at an angle to that shown in FIG. 1 such that various structures are not aligned with the direction of the web process, although this would make the manufacturing more complicated and expensive.

Figure 4:
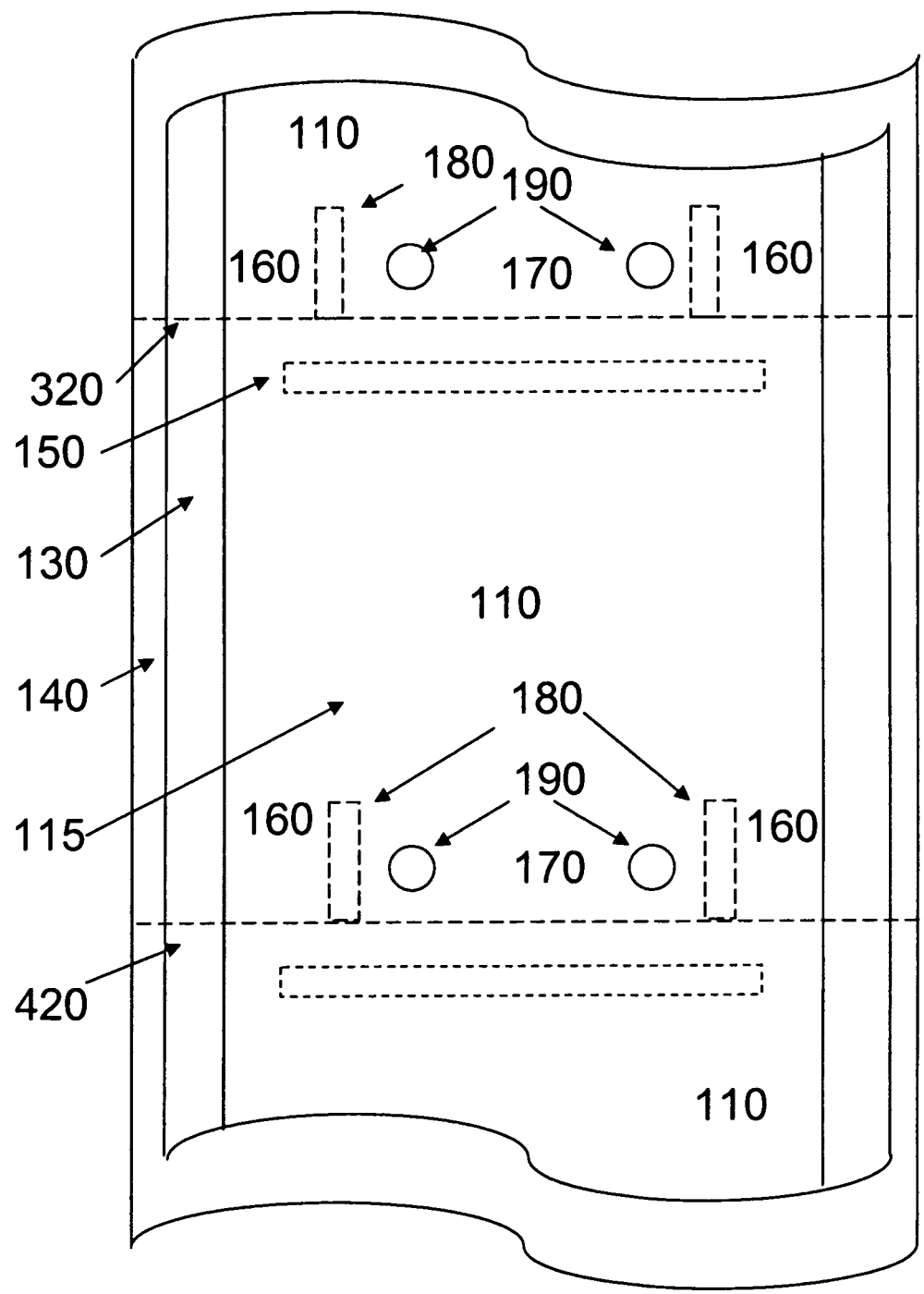
FIG. 4 illustrates a front view of an embodiment of the invention in which the masks and carrier are commonly perforated.

Masks 110 are shown as smaller in dimensions than the individual sheets of carrier material 140. However, the invention is not so limited, and the edges of masks 110 may be coextensive with any or all of the edges of carrier material 140. Such an embodiment of the invention is shown with respect to FIG. 3. In the embodiment of FIG. 1, the respirator masks 110 were not directly connected to each other on the carrier material 140. In FIG. 4, the flexible media 115 of masks 110 is formed as a continuous sheet, and commonly perforated with carrier material 140 along line 420, such that masks 110 share two common edged with the individual sheets of carrier material 140. Other deformations other than or in addition to perforations may also be used, e.g., scoring, creasing, notching.

Masks 110 are preferably on the order of a height of 5-6 inches and a width 7-8 inches, although other dimensions could be used.

According to another embodiment of the invention, carrier material 140 could be eliminated entirely if an appropriate media 115 is used for mask 110. In this case, masks 110 would be wound directly over each other to form the continuous roll. Media 115 would likely need to include at least two different layers, one on the inward (users' face side) of the mask 110 to support the adhesive, and one on the outward side of the mask 110 that would lightly bond with and easily release from the adhesive. Both layers would also need to be air permeable, and either individually or collectively with whatever purification standard was desired (e.g., N95).

It is noted that the foregoing examples have been provided merely for the purpose of explanation and are in no way to be construed as limiting of the present invention. While the present invention has been described with reference to certain embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A respirator mask dispensing system, comprising:
   a carrier material;
   a plurality of respirator masks mounted in parallel on the carrier material by an adhesive;
   the carrier material being deformed between adjacent ones of the plurality of respirator masks, the deformation being configured to assist in the tearing of the carrier material at points of deformation; and
   a central core member;
   wherein the carrier material with the plurality of respirator masks as mounted therein is wound on the central core member to provide a continuous roll; and
   wherein the adhesive bonds more strongly with the respirator masks than the carrier material such that when an individual respirator mask is removed from the carrier material the adhesive will separate from the carrier material and remain attached to the individual respirator mask.

2. The dispensing system of claim 1, wherein the individual respirator mask is dispensed by unrolling the carrier material to extend the individual respirator mask from the continuous roll, tearing the carrier material along the adjacent deformation to release a single sheet of carrier material with the individual respirator mask thereon, and separating the individual respirator mask from the torn single sheet of carrier material.

3. The dispensing system of claim 1, further comprising:
   the adhesive being positioned on the plurality of masks at least as strips with uniform thickness along the lateral sides of the plurality of masks.

4. The dispensing system of claim 3, wherein the strips are parallel to the dispensing direction of the continuous roll.

5. The dispensing system of claim 1, further comprising:
   the adhesive being positioned on the plurality of masks as at least one island proximate to an under the chin portion on the plurality of masks.

6. The dispensing system of claim 1, further comprising;
   each of the plurality of masks having first and second notches proximate to an under the chin portion of the masks that separates the under the chin portion of the masks into first, second and third sections, the second section being coextensive with an area under the chin of a wearer;
   wherein the first and third sections can be at least partially overlapped onto the second section to form a seal on a lower jaw of a wearer.

7. The dispensing system of claim 1, further comprising:
   each of the plurality of masks having a wire generally disposed in a bridge of nose portion of the masks, the wire being deformable.

8. The dispensing system of claim 7, wherein the wire is perpendicular to the dispensing direction of the continuous roll.

9. The dispensing system of claim 1, wherein the individual respirator mask is dispensed by unrolling the individual respirator mask and underlying carrier material, tearing the underlying carrier material along the adjacent deformation to release the individual respirator mask with a corresponding sheet of carrier material, and individually sealing the individual respirator mask with a corresponding sheet of carrier material within packaging.

10. The dispensing system of claim 1, wherein the plurality of respirator masks as mounted on the carrier material are separated from each other.

11. The dispensing system of claim 1, wherein the plurality of respirator masks are connected to each other, and delineated by deformations configured to assist in tearing an individual respirator mask free from the plurality of respirator masks.

12. The system of claim 1, where the deformation includes perforations.

13. The system of claim 1, where the deformation include notches in the lateral sides of the carrier material.

* * * * *